US00PP31274P2

(12) United States Plant Patent
Hansen

(10) Patent No.: US PP31,274 P2
(45) Date of Patent: Dec. 24, 2019

(54) **X *MANGAVE* PLANT NAMED 'BLAZING SADDLES'**

(50) Latin Name: ***Agave* times x *Mangave* hybrid**
Varietal Denomination: Blazing Saddles

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/351,000

(22) Filed: Feb. 11, 2019

(51) Int. Cl.
*A01H 5/00* (2018.01)
*A01H 6/12* (2018.01)

(52) U.S. Cl.
USPC ..... Plt./373

(58) Field of Classification Search
USPC ..... Plt./373
CPC ..... A01H 5/00; A01H 6/12
See application file for complete search history.

*Primary Examiner* — Annette H Para

(57) ABSTRACT

A new and unique x *Mangave* plant named 'Blazing Saddles' characterized by a rounded mound of fleshy, short, fleshy, linear to lanceolate leaves that develop concentrated reddish to greyed reddish-purple spotting with intense light. The leaves have numerous small, flexible marginal teeth pointing outwardly to recurving toward base. The new plant is suitable for the garden or as a potted plant in the garden or home.

2 Drawing Sheets

Botanical classification: *Agave* times x *Mangave* hybrid; Variety denomination: 'Blazing Saddles';

STATEMENT REGARDING PRIOR DISCLOSURES UNDER 37 CFR 1.77(B)(6)

The first public disclosure of the claimed plant, in the form of a private sale, was made by Walters Gardens, Inc. on Feb. 12, 2018 to Plant Delights Nursery, Inc. Plants for this sale were obtained from the inventor. No plants of x *Mangave* 'Blazing Saddles' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Blazing Saddles' that was hybridized by the inventor at a wholesale perennial nursery in Zeeland, Mich., USA as a cross between a proprietary unnamed selection of *Agave nizandensis* (not patented) as the female or seed parent times and x *Mangave* 'Bloodspot' (not patented) as the male or pollen parent. The cross was performed Jul. 10, 2014 and seeds were harvested and sown later the following autumn. Through trials at the same nursery the plant was assigned the breeder code 14-171-15. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Blazing Saddles' differs from its parents as well as all other *Manfreda, Agave* and x *Mangave* known to the applicant. The female parent has a flatter habit with fewer leaves per plant, with narrow, longer, aching foliage that has small marginal teeth, moderately channeled or concavo-convex with a lighter chartreuse in the center along midrib, but the leaves do not have reddish spots or nearly whole leaves. The male parent is more upright in habit with greater number of leaves per plant, with foliage that is shorter, more glaucous, thicker (abaxial to adaxial), dark brown around the marginal teeth and larger terminal spines and fewer, less-overlapping, mahogany spots. The nearest comparison plants are: 'Racing Stripes' U.S. Plant patent application Ser. No. 16/350,624, 'Red Wing' copending U.S. Plant Patent Application, 'Freckles and Speckles' U.S. Plant patent application Ser. No. 15/932,464, 'Mission to Mars' U.S. Plant Pat. No. 29,393. 'Racing Stripes' is a taller plant with dark green margins, chartreuse midrib and no reddish coloration. 'Red Wing' has more leaves per plant that are broader and the reddish coloration is more of cherry-red. 'Freckles and Speckles' has more arching foliage with spots that are more separated. 'Mission to Mars' is a much larger plant with longer and broader foliage of more uniform burgundy coloration.

'Blazing Saddles' is unique from all of the above cultivars and all *Agave*, x *Mangave* and *Manfreda* known to the inventor by the following combined traits:

1. Rounded mound of linear to lanceolate, short, sarcous leaves;
2. Leaves develop dense reddish to greyed reddish-purple spotting with strong ultraviolet light;
3. Leaf margins have many, small, flexible, outward to recurved, marginal teeth;
4. Moderate growth rate;
5. Foliage is upright to outwardly toward stem and arches with age.

BRIEF DESCRIPTION OF THE DRAWING

The photograph of x *Mangave* 'Blazing Saddles' demonstrates the overall appearance of the new plant including the unique traits as three-year-old plants grown in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
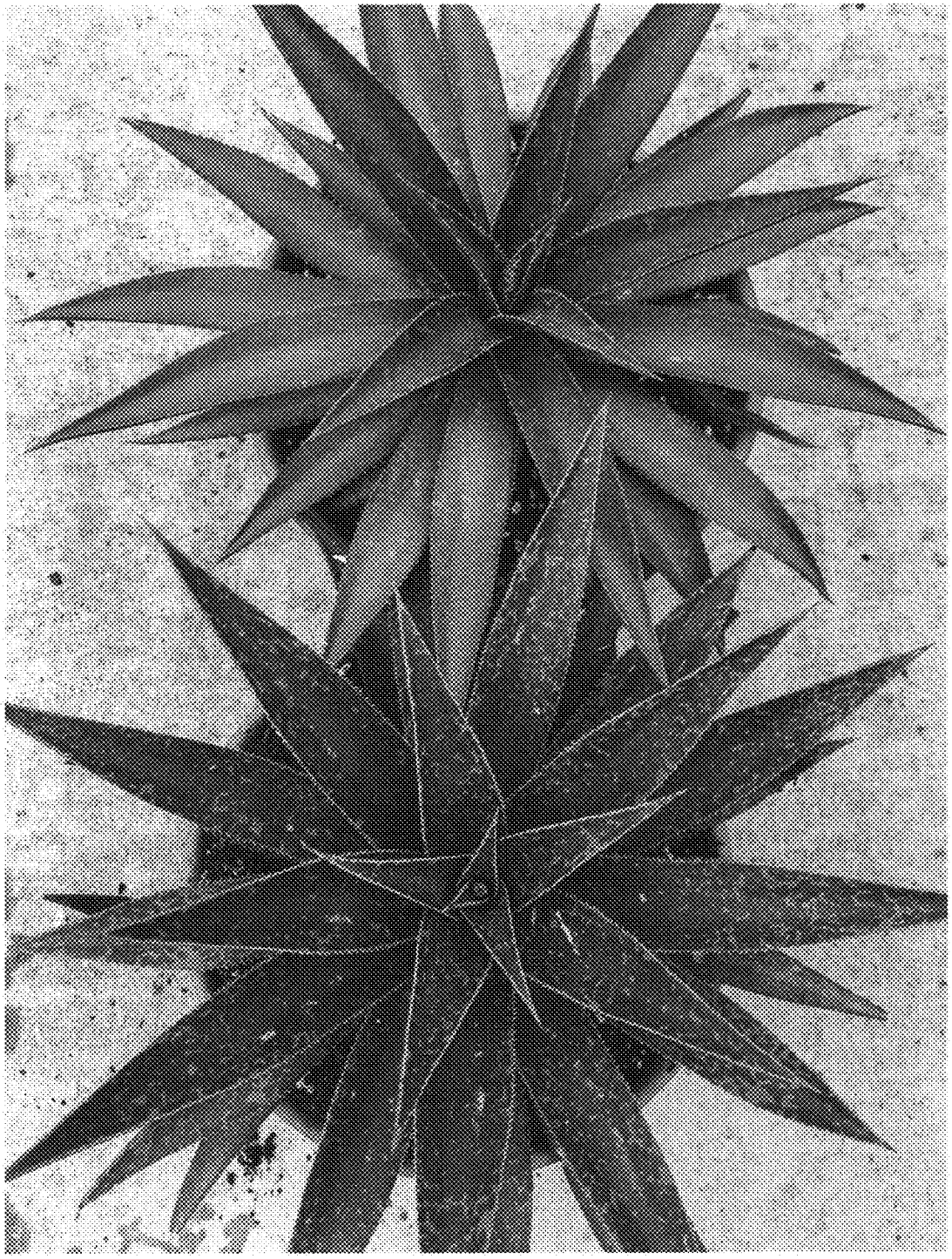
FIG. 1 shows an opaque greenhouse grown plant above with a plant grown in full-sun below.
Figure 2:
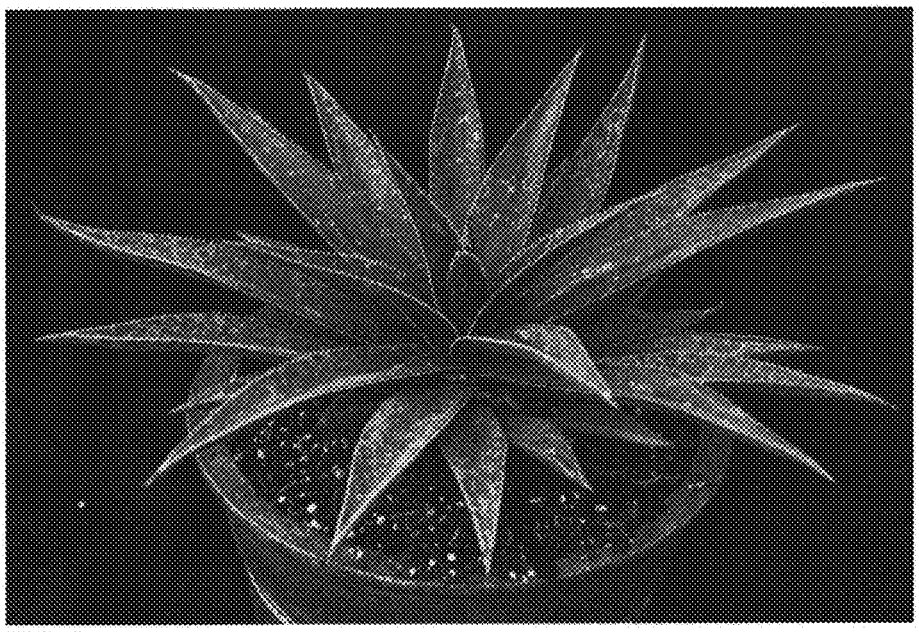
FIG. 2 shows a clear plastic greenhouse grown plant from side profile.
Figure 3:
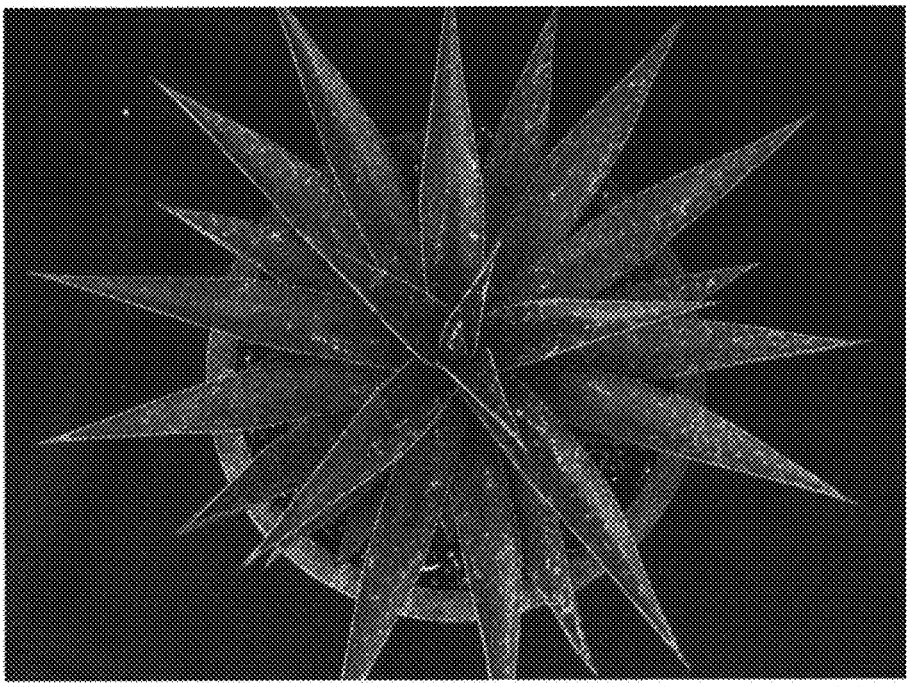
FIG. 3 shows a clear plastic greenhouse grown plant from above.

The following descriptions and color references are based on the 2015 edition of The Royal Horticultural Society Colour Chart except where common dictionary terms are used. The new plant, x *Mangave* 'Blazing Saddles', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: A proprietary unnamed selection of *Agave nizandensis* as female or seed patent and x *Mangave* 'Bloodspot' as the male or pollen parent;

Propagation: By sterile shoot-tip tissue culture and removal of basal offsets;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 30 cm long;

Root color: Nearest RHS NN155B;

Plant shape and habit: Succulent herbaceous perennial with basal rosettes of about 36 leaves radially emerging outwardly from central stem, producing a radially-symmetrical, rounded mound;

Plant size: Foliage height about 18.0 cm tall from soil line to the top of the leaves and about 39.0 cm wide at the widest point just above soil level;

Stem: To about 2.5 cm across; covered with leaves;

Foliage description: Linear to lanceolate; simple; sessile; bi-laterally symmetrical; sarcous; apex narrowly acute with firm terminal spine; base truncate; flat in proximal portion of leaf tending toward slightly concavo-convex distally; margins flat; margins finely toothed with small, flexible, outwardly to recurved teeth; glabrous abaxial and adaxial; matte abaxial and adaxial;

Terminal spine size: To about 4.0 mm long and 1.0 mm wide at base;

Marginal teeth size: About 1.5 mm long and 1.0 mm wide at base, average spacing about 1.8 mm apart;

Leaf size: To about 19.0 cm long, about 31.0 mm wide toward middle; center base about 11.0 mm thick at basal midrib; average about 17.0 cm long, 29.0 mm wide and 10.0 mm thick in longitudinal center; spots on both adaxial and abaxial vary from 1.0 mm diameter to nearly solid red with intense light;

Foliage fragrance: None observed;

Leaf number: About 36 per plant;

Leaf blade color:

*Adaxial* (*low light*).—Between RHS 148B and RHS 137C with spots between RHS 187B and RHS N187B.

*Abaxial* (*low light*).—Variable with nearest RHS 137C with spots of nearest RHS NN137B.

*Adaxial* (*high light*).—Small green patches nearest RHS 137B and reddish portion between RHS N187A and RHS 187B distally and proximally and along midrib nearest RHS 187A blended with RHS 186A, becoming nearest RHS N187A distally with highest light intensity.

*Abaxial* (*high light*).—Small green patches nearest RHS 137B and reddish portion nearest RHS 187B distally and proximally nearest RHS 187B blended with RHS 186A.

*Teeth*.—Nearest RHS 160D on older leaves, nearest RHS 158B on younger leaves.

*Terminal spine*.—Between RHS 166B and RHS 165A.

Petiole: Leaves sessile;

Veins: Parallel; not distinct abaxial or adaxial;

Flower description: Not yet observed;

Fruit and seed not observed;

Disease resistance: x *Mangave* 'Blazing Saddles' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Blazing Saddles' as herein described and illustrated.

* * * * *